United States Patent [19]

Horikoshi et al.

[11] Patent Number: 5,439,680
[45] Date of Patent: Aug. 8, 1995

[54] CELL-ASSOCIATED GLUCOSYLTRANSFERASE, AN ANTIBODY THERETO, AND A DENTAL CARIES PROPHYLACTIC COMPOSITION CONTAINING SAID ANTIBODY AS AN EFFECTIVE COMPONENT

[75] Inventors: Toshio Horikoshi, Odawara; Junichiro Hiraoka, Yokohama; Isamu Fujita, Ikeda; Tohru Tokoro, Gifu; Yoshikatsu Kodama, Gifu; Hideaki Yokoyama, Kakamigahara, all of Japan

[73] Assignees: Kanebo Ltd., Tokyo; Ghen Corporation, Gifu, both of Japan

[21] Appl. No.: 353,257

[22] Filed: Dec. 2, 1994

Related U.S. Application Data

[60] Continuation of Ser. No. 48,941, Apr. 20, 1993, abandoned, which is a continuation of Ser. No. 866,206, Apr. 9, 1992, abandoned, which is a division of Ser. No. 807,746, Dec. 17, 1991, Pat. No. 5,281,524, which is a continuation of Ser. No. 298,546, Jan. 18, 1989, abandoned.

[30] Foreign Application Priority Data

Jan. 22, 1988 [JP] Japan .................................. 63-010853

[51] Int. Cl.⁶ .................... A61K 39/395; A61K 39/40; C07K 16/02; C07K 16/12
[52] U.S. Cl. .............................. 424/157.1; 424/165.1; 530/389.5; 530/853; 435/193; 435/885
[58] Field of Search ............................. 530/389.5, 853; 424/157.1, 165.1; 435/193, 885

[56] References Cited

U.S. PATENT DOCUMENTS

| | | | |
|---|---|---|---|
| 4,150,116 | 4/1979 | Taubman et al. | 424/88 |
| 4,693,888 | 9/1987 | Miyahara et al. | 424/49 |
| 4,722,899 | 2/1988 | Hamaoka et al. | 435/172.2 |
| 4,725,428 | 2/1988 | Miyahara et al. | 424/50 |
| 4,748,018 | 5/1988 | Stolle et al. | 424/87 |
| 4,933,182 | 6/1990 | Higashi et al. | 424/435 |
| 5,281,524 | 1/1994 | Horikoshi et al. | 435/193 |
| 5,281,746 | 1/1994 | Chou et al. | 560/155 |

FOREIGN PATENT DOCUMENTS

| | | |
|---|---|---|
| 60-38327 | 2/1985 | Japan . |
| 60-248628 | 12/1985 | Japan . |
| 63-10853 | 1/1988 | Japan . |
| 1505513 | 3/1978 | United Kingdom . |

OTHER PUBLICATIONS

Molecular Microbiology and Immunobiology of *Streptococcus mutans* Mukasa et al. pp. 121–132 "Properties of *Streptococcus mutans* Glucosyl Transferases" 1986.

Infection and Immunity, Jul. 1974 pp. 227–235 vol. 10, No. 1, pp. 227–235 Kuramitsu for "Characterization of Cell-Associates Dextransucrase Activity from Glucoseo-Grown Cells of *Streptococcus mutans*".

Infection and Immunity, Jan. 1983, vol. 39 No. 1, pp. 43–49 Ooshima et al. "Non α Cariogenicity of the Disaccharide Palatinose in Experimental Dental Caries of Rats".

J. Dent Res 63(3): Mar. 1984, pp. 407–411, Hamada et al. "Virulence Factors of *Streptococcus mutans* and Dental Caries Prevention".

Gunn et al., Journal of Virology, vol. 54, No. 3, pp. 791–797 (1985).

Kuramitsu, Infections and Immunity, vol. 12, pp. 738–749 (1975).

Hamada et al., Journal of General Microbiology, vol. 135, pp. 335–344 (1989).

(List continued on next page.)

*Primary Examiner*—Christina Y. Chan
*Attorney, Agent, or Firm*—Nixon & Vanderhye

[57] ABSTRACT

Cell-associated glucosyltransferase of *S. mutans* serotypes c, e or f producing dental caries was isolated and purified and its characteristics as an enzyme were revealed. Furthermore, an antibody against said enzyme was prepared from eggs of the hens immunized with said enzyme. Since this antibody effectively prevents adherence of the aforementioned *S. mutans* to tooth surfaces, it is useful as an effective component for a dental caries prophylactic composition.

16 Claims, 3 Drawing Sheets

OTHER PUBLICATIONS

Kuramitsu et al., Infection and Immunity, vol. 13, pp. 1775–1777 (1976).

FEMS Microbiology Letters 16 (1983) 159–162 Kenney et al. "Identification of 1,3- . . . mutans".

Carbohydrate Research, 134 (1984) 293–304 Sato et al. "Isolation and some Properties of Extracellular . . . mutans serotypes c, e, and f".

Biol vol. 34, pp. 399–402 Hamada et al. "Synthesis and Binding of Glucosyltransferase and in vitro . . ." (1979).

Carbohydrate Research, 158 (1986) 147–155 Baba et al. "Purification and Characterisation of the extracellular . . . mutans".

Infection and Immunity Nov. 1983 pp. 763–770 vol. 42 No. 2 Kuramitsu et al. "Insoluble Glucan Synthesis by . . . c Strains".

Analytical Biochemistry 72, 248–254 (1976) Bradford "A Rapid and Sensitive Method for the Quantitation of . . . Binding".

Ma et al, Infection & Immunity, 55, pp. 1274–1278, May 1987.

Kuramitsu et al. Arch. Oral. Biology, vol. 23, pp. 691–696 (1978).

Goodman, Basic & Clinical Immunology, Fiedenberg et al. (ed.) Lange Medical Publications, Los Altos, Calif., pp. 32–40 (1976).

Russell et al., Archs Oral Biol. vol. 26 pp. 23 to 28 1981.

Hamada et al., Infection and Immunity, vol. 59, No. 11, Nov. 1991 pp. 4161–4167.

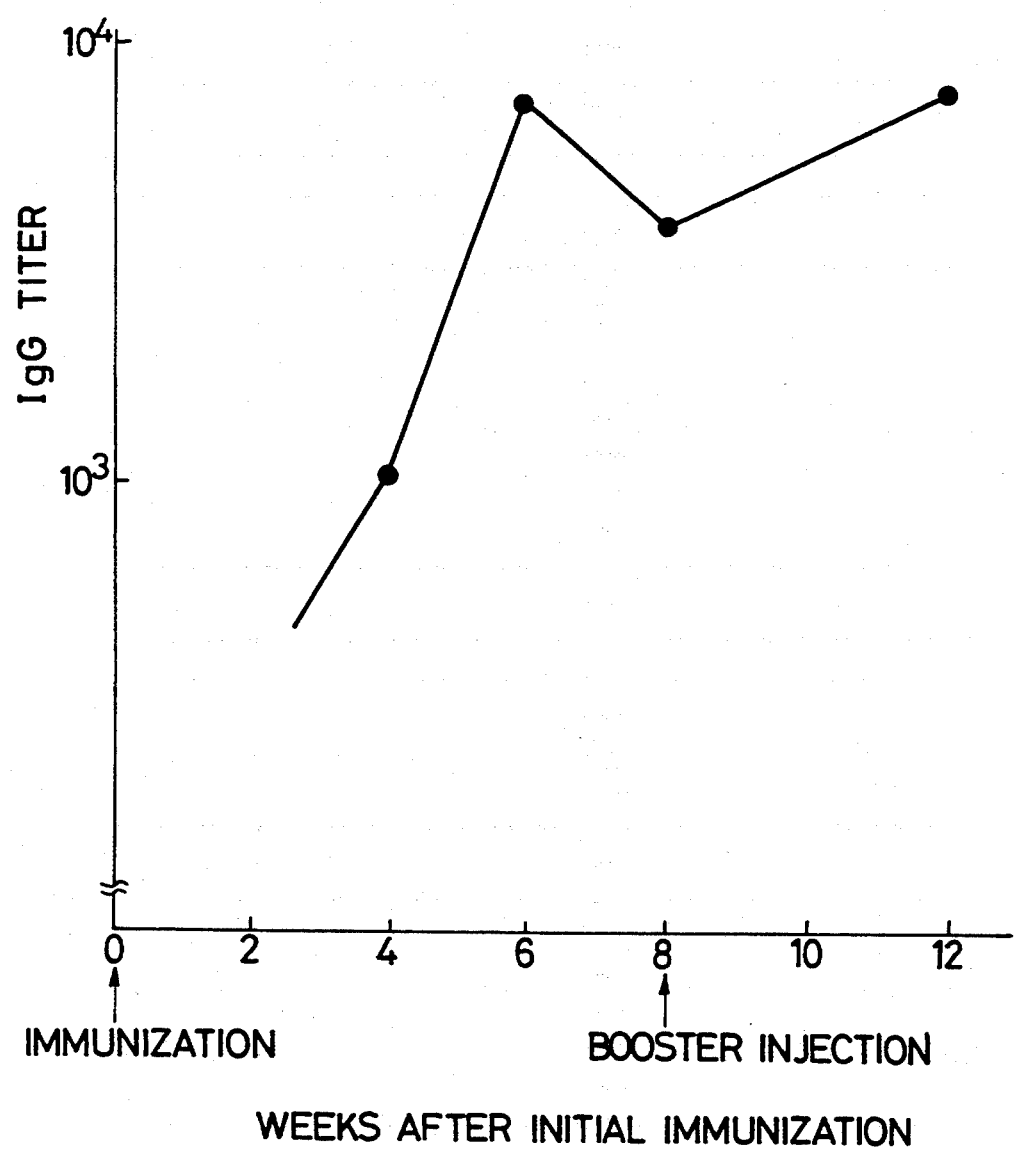

CELL-ASSOCIATED GLUCOSYLTRANSFERASE, AN ANTIBODY THERETO, AND A DENTAL CARIES PROPHYLACTIC COMPOSITION CONTAINING SAID ANTIBODY AS AN EFFECTIVE COMPONENT

This is a Rule 62 File Wrapper continuation of application Ser. No. 08/048,941, filed Apr. 20, 1993, now abandoned which is a continuation of Ser. No. 07/866,206 filed Apr. 9, 1992, now abandoned which is a division of Ser. No. 07/807,746 filed Dec. 17, 1991 now U.S. Pat. No. 5,281,524 which is a continuation of application Ser. No. 07/298,546 filed Jan. 18,1989, abandoned

BACKGROUND OF THE INVENTION

1. Field of the Invention

The present invention relates to cell-associated glucosyltransferase which reacts with sucrose and catalyzes a reaction of synthesizing water-insoluble glucans, to a method of purifying this enzyme and to a method of producing this enzyme.

The present invention also relates to an antibody having immunological activity against *Streptococcus mutans* which is known as pathogenic bacteria inducing dental-caries and to a dental caries prophylactic composition which contains said antibody as an effective component.

2. Description of the Prior Art

In view of dental caries prophylaxis, a number of investigations have been undertaken to elucidate the properties of *S. mutans* known as causative bacteria for dental caries and the mechanism of involvement of said bacteria in the development of dental caries.

As to *S. mutans* strains which are involved in the development of dental caries, eight strains, being classified serologically into serotypes a to h, have now been found. Of these serotypes, two subgroups have been defined on the basis of the serological analogy, serotypes d and g in one group and serotypes c, e and f in the other group.

It is already known that the important process in the mechanism of the involvement of *S. mutans* in developing dental caries is the process of producing adherent, water-insoluble glucans from sucrose, in which glucosyltransferase (hereinafter referred to as GTF) produced by *S. mutans* plays a part.

This GTF produced by *S. mutans* can be found either in the culture supernatant or on the cell surface in an associated form.

For example, in the culture of strains of serotype d or g, serologically analogous one another, in the absence of sucrose, GTF is present mostly in the culture supernatant, from which three kinds of GTF, namely GTF-S1, GTF-S2 and GTF-I, have now been isolated and purified (S stands for a water-soluble glucan synthesizing enzyme and I stands for a water-insoluble glucan synthesizing enzyme). These three kinds of GTF cooperatively produce adherent, water-insoluble glucans (see, for example, "Synthesis of glucans by *Streptococcus mutans* and adherence mechanisms", T. Koga, Jap. J. Bacteriol., 41 (4), 679, 1986).

Further, in the culture of the strains of serotypes d and g in the presence of sucrose, it is known that the aforementioned three kinds of GTF are mostly bound to the cells by binding to glucans to give cell-associated forms (Hamada, S. and Slade, H. D., Archs Oral. Biol., 24, 399–402, 1979).

On the other hand, GTF-S and GTF-I have been isolated also from the culture supernatant of the strains of serotypes c, e and f, serologically analogous one another (Kuramitsu, H. K. and Wondrack, L., Infect. Immun., 42, 763–770, 1983).

However, there has been no single report that water-insoluble, adherent glucans can be synthesized in joint action of these GTF-S and GTF-I.

Furthermore, attempts have been made to develop methods or agents for preventing dental caries, making *S. mutans* a target organism. A known example of the method of preventing dental caries by controlling the colonization of *S. mutans* in the oral cavity (especially by controlling the adherence to tooth surfaces) is the method for dental caries prevention by using antibodies which have immunological activity against *S. mutans*. Namely, a method of preventing the colonization of *S. mutans* in the oral cavity by using milk obtained from cows which are immunized by cells of *S. mutans* has been disclosed in British Patent Specification No. 1505513, and a dental caries preventive agent which is a combination of antiserum and/or milk obtained from the mammalian having been immunized by a fraction such as cell walls recovered from the culture of *S. mutans* and one or more of the synergists selected from the group consisting of glucosyltransferase inhibitors, proteases and dextranases has been disclosed in the specification of Japanese Patent Laid Open No. 60-38327.

However, the effect of preventing dental caries by the antibodies having immunological activity against *S. mutans* is not always satisfactory. Furthermore, since the antibodies are conventionally prepared from milk or antiserum of immunized mammalians, in many cases, they are not practically produced owing to such disadvantages as inappropriateness to mass production or high production cost.

SUMMARY OF THE INVENTION

In order to establish technologies for more effective prophylaxis of dental caries, the present inventors have been paid their attentions to serotype c strains which are distributed most prevalently in the human oral cavity and seem to have the most important role in developing human dental caries, as well as to strains of serotypes e and f, serologically analogous to serotype c strains. In the course of various investigations to elucidate the mechanisms of the involvement of these strains in developing dental caries, present inventors have isolated and purified GTF fractions which play roles in the process of synthesizing water-insoluble glucans produced by these bacteria. The investigations have been furthermore proceeded from a point of view that the elucidation of the properties of the GTF is important.

As a result, the present inventors have confirmed the presence of cell-associated GTF, among the GTF fractions produced by these bacteria, having water-insoluble glucan synthesizing enzyme activity (hereinafter referred to as CA-GTF-I), which may have an important role in adherence of the bacteria to tooth surfaces, especially in sucrose dependent adherence. In consequence, the present inventors have attempted the isolation and purification of the CA-GTF-I.

Further, in conventional techniques, isolation of cell-associated types of GTF (-I) of strains of sertypes c, e or f as a purified enzyme protein have not been successfully accomplished up to now so as to thoroughly investigate their properties.

For example, as to the cell-associated GTF-I produced by a serotype c strain, there is a report by Kuramitsu (Kuramitsu, H. K., Infect. Immun., 10, 227–235, 1974). Namely, Kuramitsu et al. obtained an extract having water-insoluble glucan synthesizing enzyme activity from the cells by using 1M NaCl and investigated the properties of the extract as GTF. In this, it is reported that the pH optimum was 6.0 and the temperature optimum was 37° C. for GTF activity in the extract.

However, since the extract obtained by Kuramitsu becomes water-insoluble when subjected to desalting treatment necessary in purification procedures, the acquirement of a purified protein fraction having GTF activity from the extract has not been substantially successful. Hence, the data provided by Kuramitsu concerning the cell-associated GTF fraction were not based on a purified enzyme protein fraction and were accordingly esteemed to be extremely insufficient to specify the enzyme having GTF activity. Especially, the enzyme contained in the fraction extracted from the cells has not at all characterized as a enzyme protein. Namely, none of the characteristics such as a molecular weight or an isoelectric point has been demonstrated.

On the other hand, it has been demonstrated by Kenney et al. and Kuramitsu et al. that GTF-I of serotype c strains is present in the culture supernatant fractions.

Kenney et al. have demonstrated that GTF-$I_c$, with a molecular weight of 153 k daltons, having activity to synthesize water-insoluble polysaccharides is present in the culture supernatant of a serotype c strain (A. C. Kenney and J. A. Cole, FEMS Microbiol. Lett., 16, 159–162, 1983).

However, Kenney et al. have demonstrated only the presence of the GTF-$I_c$ in the culture supernatant, and neither the information on the isolation and purification of the enzyme nor the data necessary to specify characteristics of the enzyme as a protein has been provided.

On the other hand, Kuramitsu et al. have isolated, from the culture supernatant of a c type strain, a fraction containing dextransucrase (DS, GTF-$S_c$) having activity to synthesize water-soluble glucans and a fraction containing mutansynthetase (MS, GTF-$I_c$) having activity to synthesize water-insoluble glucans, and then carried out various analyses, for example, for GTF activity, of these fractions to demonstrate that DS and MS were two different enzymes. The obtained MS had the immunogenicity different from that of DS, and had a molecular weight of 155 k daltons and an isoelectric point (pI) of 4 to 5 (Kuramitsu, H. K. and Wondrack, L., Infect. Immun., 42, 763–770, 1983).

Under these circumstances, the present inventors have been made several efforts in investigating a process for isolating and purifying CA-GTF-I in order to confirm the presence of this enzyme. As a result, the present inventors have succeeded in isolating and purifying CA-GTF-I from cells of serotype c bacteria for the first time and obtained novel information on its characteristics so as to accomplish the present invention.

Furthermore, the present inventors have acquired novel information that an antibody against CA-GTF-I thus isolated and purified has sufficient effect in preventing adherence of S. mutans to tooth surfaces and that the antibody can be produced at low cost in large scale by means of immunizing hens with the purified CA-GTF-I as an antigen, so as to accomplish the present invention.

One object of the present invention is to provide CA-GTF-I as a water-insoluble glucan synthesizing enzyme which is useful in developing more efficient techniques and various medicinal agents necessary for elucidation of detailed mechanism of the development of dental caries or for prophylaxis of dental caries.

Another object of the present invention is to provide an antibody which has immunological activity against S. mutans, has sufficient preventive effect on adherence of S. mutans to tooth surfaces and is useful as an effective component of a dental caries prophylactic composition.

Another object of the present invention is to provide a method of producing the antibody at low cost in a large scale.

Another object of the present invention is to provide a dental caries prophylactic composition containing the antibody as an effective component.

BRIEF DESCRIPTION OF THE DRAWINGS

FIG. 3 shows the changes in the antibody titer of immunized hens in Example 3.

DETAILED DESCRIPTION OF THE PREFERRED EMBODIMENTS

Figure 1:
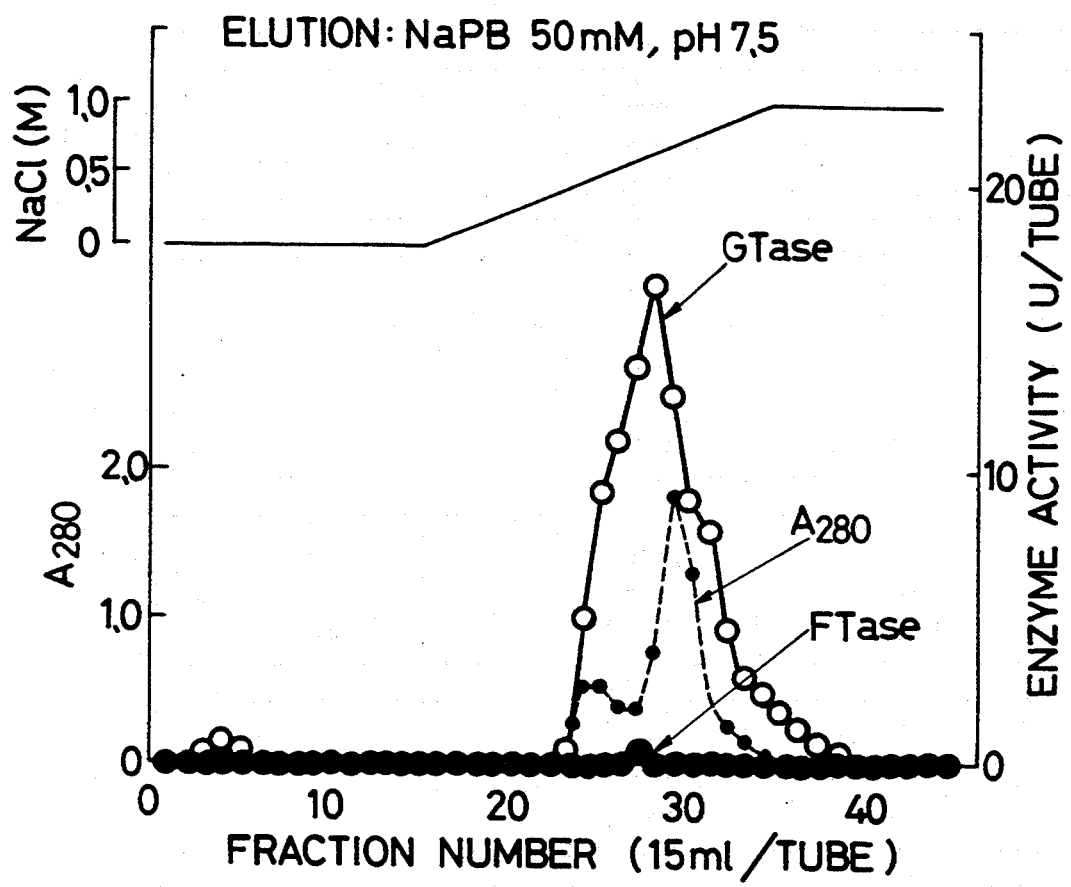
FIG. 1 shows the protein concentration ($A_{280}$), GTF activity and FTase (D-fructosyltransferase) activity in the factions eluted from DEAE-SEPHACEL in Example 3.

The isolated cell-associated glucosyltransferase (CA-GTF-I) of the present invention has at least the following physicochemical characteristics.

(1) Reaction and substrate specificity: Reacts with sucrose and produces water-insoluble glucans.

(2) pH optimum: pH 6.7–7.0

(3) Range of temperature optimum: 15°–50° C.

(4) Inactivation conditions: Inactivated by heating at 80° C. for 5 minutes.

(5) Molecular weight: 150 k–165 k daltons measured by SDS-polyacrylamide gel electrophoresis.

(6) Immunogenicity: Immunogenic in animals so as to induce production of specific antibody against the enzyme.

Also in view of the fact that the pH optimum for GTF activity of CA-GTF-I is approximately the same as the pH in the oral cavity as described above, it is readily understood that CA-GTF-I may play an important role in the behavior of S. mutans in the oral cavity.

As CA-GTF-I is capable of being immunogenic in animals as described above, the specific antibody against the enzyme can be produced by administering the enzyme to animals. The antibody thus obtained is useful in the field of preventing dental caries as mentioned above.

Furthermore, CA-GTF-I can be efficiently applied for producing glucans from sucrose.

The enzyme activity of CA-GTF-I may be determined, for example, by measuring the amount of incorporation of radio activity into glucans produced in the reaction of the enzyme with [$^{14}$C-glucose] sucrose as a substrate.

One unit (U) of GTase activity is defined as the amount of enzyme required to incorporate 1.0 micromol of glucose residue from the sucrose molecule into glucan per min.

CA-GTF-I can be obtained, for example, by isolating and purifying GTF-I produced in a cell-associated form, from the cells.

As evidently described in the Examples thereinafter, CA-GTF-I is distinctly different from GTF-S (CF-GTF-S) which is present in the supernatant of the culture of serotype c bacteria and has an activity to synthesize water-soluble glucans.

CA-GTF-I according to the present invention can be isolated and purified from the bacteria of strains of serotypes c, e or f in the manner as described below.

Firstly, the cells of serotypes c, e or f are cultivated in an appropriate medium and the resultant cells are collected, and washed, if necessary.

The strains of serotype c to be used here are, for example, S. mutans strain MT8148, strain Ingbritt and strain NCTC 10449.

Further, these strains are publicly known and readily available.

For example, S. mutans strain MT8148 and strain Ingbritt are obtainable from the Department of Dentistry, Osaka University and strain NCTC 10449 is obtainable from American Type Culture Collection (ATCC) as strain ATCC 25175. Further, as to the strains of serotypes e and f, any of the publicly known, available strains may be used.

As to the culture media, any of the media containing, at least, glucose can be used. For example, TTY medium (a complex medium composed of Trypticase, Tryptose and Yeast extract), BHI (Brain Heart Infusion) medium and FMC medium may be used.

Furthermore, the cultivation may be conducted at any temperature ranges in which appropriate bacterial growth and CA-GTF-I production be expected. However, in terms of the sufficient bacterial growth and CA-GTF-I production, the temperature of approximately 37° C. may be generally employed.

The time required for cultivation varies according to cultivation conditions, such as the cultivation temperature and kind of medium used. The incubation time to reach optimal yield of CA-GTF-I may be advantageously selected. In general, 18 to 20 hours may be employed.

Further, other cultivation conditions may be appropriately selected from viewpoints described above.

Next, CA-GTF-I is extracted from the cells.

The extraction of CA-GTF-I from the cells can be carried out, for example, by a method in which the cells are allowed to contact with the extracting solution, such as urea solution and guanidine-HCl solution.

The extraction conditions such as the concentration of cells suspended in the extracting solution, the concentration of the extracting solution, the temperature and time for the extraction, may be appropriately selected according to the kind of the extracting solution so that sufficient extraction of the desired enzyme be possible.

Further, in order to obtain the extract having high specific activity in high yield, urea solution of preferably 6 to 10M, more preferably 8M, was used. The extraction may be carried out preferably at 20° to 30° C., more preferably at 25° C., for about 15 minutes to 2 hours.

After the extraction, solid components such as cells were removed from the extract, for example, by centrifugation. The resultant supernatant was then treated by means of procedures, such as dialysis, ultrafiltration or gel filtration, to remove urea, low molecular weight impurities or the like from the extract, so as to obtain a crude extracted preparation of CA-GTF-I.

Further, in the case where precipitates were formed during such a treatment as dialysis, they may be removed, for example, by centrifugation.

Furthermore, the crude extracted preparation can be purified to obtain a purified CA-GTF-I preparation.

For this purification, various purification methods generally used for enzyme purification may be applicable. For example, as hereinafter described, a method of combination of two adsorption procedures, one with an anion exchanger and the other with hydroxylapatite, can be advantageously applied.

An example of the anion exchanger used for the purification of the crude extract preparation is that having functional residues such as diethylaminoethyl (DEAE) group, and more specifically, DEAE-SEPHACEL (Pharmacia) can be used.

An example of the hydroxylapatite to be used is BIO-GEL HTP (Bio-Rad Laboratories).

In the purification procedure with an anion exchanger, extracted components (crude protein components) contained in the crude extracted preparation are applied to the anion exchanger column and then fractions containing the desired enzyme can be selectively eluted from the components adsorbed to the anion exchanger.

The fractions containing the desired enzyme can be obtained, for example, by controlling the salt concentration of the eluent.

This salt concentration varies depend on the kind of anion exchanger or the conditions for elution. The concentration may be determined by selecting the range in which the GTF(I)-containing factions can be selectively fractionated.

For example, in the case where DEAE-SEPHACEL is used, GTF(-I) can be obtained with NaCl concentrations ranging from 0.45 to 1.0M in phosphate buffer.

Further, the sample to be subjected to the contact with the anion exchanger can be prepared from the crude extracted preparation in a manner wherein a crude protein fraction is obtained by precipitating the crude extracted preparation using a solution of salt such as ammonium sulfate or an organic solvent such as ethanol, recovering the resultant precipitate by centrifugation procedure or the like, suspending the precipitate in an appropriate solvent, and then removing low molecular weight impurities from the precipitate in such a procedure as dialysis, if necessary.

After the treatment with the anion exchanger, fractions having GTF(-I) activity are pooled, desalted, for example, by dialysis and then applied to a hydroxylapatite column.

Subsequently, CA-GTF-I fraction were selectively eluted from the fraction having been adsorbed on the hydroxylapatite, pooled and, if necessary, subjected to dialysis or the like, so as to obtain a purified CA-GTF-I preparation.

The purified CA-GTF-I preparation thus obtained gives a single band corresponding to those with the molecular weight of 150 k to 160 k daltons on an SDS-PAGE gel.

Furthermore, according to the procedures as described above, for example, such purification, the enzyme having the specific activity as high as 6.96 U/mg protein be achieved as thereinafter described in Examples.

Furthermore, CA-GTF-I in the present inventigation can be produced by the aforementioned procedures for bacterial cultivation and extraction. The resultant extract may be purified until desired purities be obtained.

An antibody having an immunogenic activity against S. mutans (anti-CA-GTF-I antibody) according to the present invention can be obtained as an immunoglobulin prepared from eggs produced by the hens immunized with the CA-GTF-I described above.

In order to prepare an antigen fluid for immunization of the hens, an example of CA-GTF-I to be applicable is that contained in the cell extract or in the crude preparation obtained by the aforementioned procedures for isolation of CA-GTF-I, or that obtained as the purified preparation.

The anti-CA-GFT-I antibody can be prepared from the eggs of hens immunized with the aforementioned CA-GTF-I.

As to the hens to be immunized, any kinds of hens can be used, but from a viewpoint of mass productivity, those of species raised for egg production, such as white leghorns can be preferably used.

Furthermore, the methods of immunization with CA-GTF-I are ordinary ones such as subcutaneous injection, intraperitoneal injection, intramuscular injection, intranasal injection and dropping in the eyes. Furthermore, the amount of dose may be appropriately selected so as to obtain desired the antibody titer and not to give any detrimental influence to the hens.

In general, in several weeks after the first immunization, an antibody which reacts extraordinarily with the antigen can be produced in the eggs (egg yolk). Further, if necessary, an adjuvants such as FCA (Freund's complete adjuvant) or FIA (Freund's incomplete adjuvant) may be used in combination with CA-GTF-I.

The anti-CA-GTF-I antibody according to the present invention can be prepared from the eggs that the hens laid about one month or more after the immunization.

Further, the antibody titer can be measured, for example, by using enzyme-linked immunosolvent assay (ELISA) or radioimmunoassay, and change in the antibody titer can be traced by measuring the antibody titer at about 2 week intervals after the immunization.

In Examples thereinafter mentioned, the change in the antibody titer is monitored by measuring with ELISA, and the eggs are collected when the antibody titer is increased sufficiently enough to prepare the anti-CA-GTF-I antibody of the present invention.

Furthermore, in general, high antibody titer can be maintained over the period of about three months.

Further, after the immunization, when the antibody titer decreased, the antibody titer can be increased by additional immunization given appropriately at appropriate intervals.

The anti-CA-GTF-I antibody according to the present invention can be obtained, for example, by extracting and isolating immunoglobulin contained in the egg yolk of hens immunized as described above.

Examples of methods to be applied for extraction and isolation include a variety of methods ordinarily used for extraction and isolation of immunoglobulins, such as precipitation methods using dextran sulfate or polyethylene glycol (PEG) and extraction methods using propanol or chloroform.

The anti CA-GTF-I antibody obtained as described above reacts as an antibody specifically with CA-GTF-I present in an associated form with the cells of S. mutans. Namely, it has immunological activity agains S. mutans.

The anti-CA-GTF-I antibody having the immunological activity against S. mutans has an effect to inhibit adherence of S. mutans to tooth surfaces. Accordingly, by administering the antibody to the oral cavity, the activity of S. mutans in the oral cavity can be controlled so as to prevent the dental caries development.

A dental caries prophylactic composition according to the present invention contains the aforementioned anti-CA-GTF-I antibody as an effective component and can be prepared in various forms according to the manner of administration to the oral cavity.

For example, when applied as a mouth wash or tooth paste, anti-CA-GTF-I antibody may be added in an effective amount to a variety of constituents in the process of preparation.

The amount of the anti-CA-GTF-I antibody to be added to the dental caries prophylactic composition can be appropriately selected according to the amount of doses suitable to the individual mode of administration. For example, about 0.0001 to 10% by weight of the antibody having the antibody titer of more than $10^3$ may be used.

The dental caries prophylactic composition according to the present invention can be provided as various articles including, for example, dentifrice, mouth wash, oral refresher, troche, chewing gum, etc. The dental caries prophylactic composition can be prepared by combining the above anti-CA-GTF-I antibody with various carriers and/or additives commonly used to prepare the articles. For its preparation, there may be employed any well-known processes used in the preparation of the articles.

The compounding ratio of the carriers and additives commonly used for the preparation of the articles may be also applied to the preparation of the composition of the present invention.

A tooth paste may be generally composed of an abrasive, a binder, a moisture retaining agent, a blowing agent and a perfume.

The examples of the abrasive include calcium secondary phosphate, calcium carbonate, calcium pyrophosphate, insoluble sodium metaphosphate, silicic acid anhydride and the like. The tooth paste may generally contain 10–95 weight % of the abrasive.

The examples of the binder include carboxymethylcellulose, sodium alginate, carrageenan and the like. The tooth paste may generally contain 0.5–4% of the binder.

The examples of the moisture retaining agent include sorbitol, glycerol, propylene glycol and the like. The tooth paste may generally contain 5–30% of the moisture retaining agent.

The examples of the blowing agent include anionic activators such as disodium lauryl sulfate, lauroyl sarcosinate and monolaulin (lauric acid monoglyceride), nonionic activators such as sucrose fatty acid ester, lauryldiethanolamide and stearic acid monoglyceride and the like. The tooth paste may generally contain 0.5–2% of the blowing agent.

In addition, the anti-CA-GTF-I antibody according to the present invention, obtained by the method using the hens as described above, has the following advantages as compared to the antibodies obtained by the immunization of conventional mammalians:

(1) The antibody according to the present invention can be produced in the eggs of the immunized hens, so that none of specific or skilled techniques is necessary in collecting or handling the eggs and in obtaining the antibody from the eggs. Moreover, among immunoglobulins, only the antibody of IgG class is transferred into the egg yolk, so that only the IgG can be easily obtained.

In contrast, in the cases where antibodies are obtained by drawing the blood from immunized mammalians, skilled techniques are necessary in drawing the blood, and besides it is yet difficult to isolate and purify a large quantity of IgG from the serum.

(2) The hens used for the preparation of the antibody according to the present invention are easily raised so that the cost for the raising is less expensive as compared to, for example, that for rats.

Moreover, the method using mammalians may not be suitable for mass production of antibodies because it is difficult to continuously obtain a large quantity of the blood or milk from mammalians. In contrast, the method according to the present invention makes it possible to produce antibodies in bulk at low cost because hens continue to constantly produce eggs over a long period of time.

(3) In many cases, stability of antibodies prepared from the blood or milk of immunized mammalians is not always satisfactory, so that the storage at the temperature about $-80°$ C. is required in the serum or even in the purified forms.

In contrast, the antibody according to the present invention exhibits excellent stability and can be well preserved so as to be stored, for example, at 4° C. for 1 to 2 months in the form of eggs.

Further, in preparation of an antibody by using hens, sufficient antibody titer is not always obtained in the cases of some types of antigens. For example, when a virus was used as an antigen, sufficient antibody titers were not obtained.

Accordingly, it has been found, for the first time, by the present inventors that an antibody having sufficiently high antibody titer can be obtained by immunizing hens with cell-associated glucosyltransferase.

EXAMPLES

The present invention will be explained in more detail in the following Examples.

EXAMPLE 1

Investigation on localization of GTF in different serotypes of S. mutans

Each of S. mutans of different serotypes given in Table 1 (obtained from the Department of Dentistry, Osaka University) was incubated individually in 50 ml each of BHI medium and TH (Todd-Hewitt) medium at 37° C. for 18 hours.

After the incubation, the cells and culture supernatant were separated by centrifugation and the resultant cells were washed with saline.

Then, individual GTF activities of the cells and the culture supernatant were measured according to the method described below. The results are given in Table 1.

Method for measuring GTF activity:
1) Samples for the measurement

In the case of cells:
The cultured cells were harvested, washed with saline, suspended in 5 ml of 10 mM phosphate buffer (pH 6.0), and then disrupted by ultrasonication treatment to obtain a cell suspension sample for the measurement. In the case of supernatant:
The culture supernatant was used without any treatment as a sample.

2) Measurement of GTF activity:
Ten microliters of each of the samples was mixed with 10 microliters of 0.2M phosphate buffer (pH 6.0) containing 20 mM of [$^{14}$C-glucose] sucrose (0.05 Ci/mol) as a substrate and allowed to react at 37° C. for 1 hour. After the reaction, all of the reaction mixtures were spotted on a filter paper square (1.0×2.0 cm) and were washed with methanol. Radioactivities incorporated into methanol-insoluble glucans remaining on the filter papers were measured to calculate GTF activities.

TABLE 1

| Strain (sero-type) | Medium | Final medium pH | GTF activity (mU/ml) Extra-cellular (EX) | GTF activity (mU/ml) Cell-associated (CA) | EX/CA |
| --- | --- | --- | --- | --- | --- |
| MT8148 | BHI | 5.6 | 10.1 | 2.4 | 4.2 |
| (c) | TH | 5.6 | 14.5 | 3.6 | 4.0 |
| MT4245 | BHI | 5.5 | 17.5 | 1.4 | 12.5 |
| (e) | TH | 5.5 | 19.5 | 2.1 | 9.3 |
| MT4251 | BHI | 5.4 | 16.7 | 1.5 | 11.1 |
| (f) | TH | 5.5 | 12.0 | 3.3 | 3.6 |
| OMZ176 | BHI | 5.8 | 13.1 | 0.5 | 26.2 |
| (d) | TH | 5.7 | 3.1 | 11.2 | 0.28 |
| 6715 | BHI | 5.9 | 11.8 | 0.2 | 59.0 |
| (g) | HI | 6.0 | 1.9 | 3.2 | 0.59 |

As evident from the results given in Table 1, as to the bacteria of serotypes d and g, in the cultures in BHI medium, namely in the absence of sucrose, most of the GTF activity are found in the supernatant, but in the cultures in TH medium, namely in the presence of sucrose, most of the GTF activity are found in the cells (in a cell-associated form).

On the other hand, as to the bacteria of serotypes c, e and f, none of such big differences as observed for those of serotypes d and g was observed.

EXAMPLE 2

Extraction of CA-GTF-I from the cells

S. mutans strain MT8148 (serotype c) was cultivated in one liter of TTY medium at 37° C. for 18 hours. The cells were harvested by centrifugation and further washed two times with saline.

Subsequently, portions of the cells were suspended in various extracting solutions and the resultant suspensions were subjected to extraction with stirring.

After finishing the extracting procedure, the cells were separated from the extracting solutions by centrifugation, and the resultant supernatant fluids were dialyzed against 10 mM phosphate buffer (pH 6.0).

After the dialysis, the impurities produced in the individual supernatant fluids were removed by centrifugation, and the GTF activities and protein concentrations in the individual supernatant fluids were measured.

Further, the GTF activity was measured by the method described in Example 1 and the protein concentration was measured by the method of Lowry et al.

using bovine serum albumin (BSA) as the standard, so as to calculate the specific activity.

Table 2 shows representative examples of the extracting solutions and the extracting conditions used in the extracting procedure and specific GTF activities of the extracts.

In addition, the cells obtained as described above were suspended in 1 mM phosphate buffer (pH 6.0) and the resultant suspensions were subjected to disruption by ultrasonic oscillation at 20 KHz and 200 W for 3 minutes to prepare cell disruption mixtures. After centrifugation to remove insoluble fractions, the resultant supernatant fluids were similarly assayed for GTF activity. The results are also given in Table 2.

TABLE 2

| Extracting method | Conditions | Specific activity (U/mg) | Recovery (%) |
|---|---|---|---|
| 8M Urea | 25° C., 1 hr | 0.98 | 95.1 |
| | 4° C., 1 hr | 0.29 | 28.8 |
| 6M Guanidine-HCl | 4° C., 1 hr | 0.44 | 52.8 |
| | | | (49.2)* |
| 1M NaCl | 4° C., 1 hr | 0.45 | 7.3 |
| | | | (19.7)* |
| Ultrasonication | 4° C., 3 min | 0.09 | 20.0 |

*Recovery of the insoluble compound produced during the dialysis procedure.

As evident from the results shown in Table 2, it was revealed that protein fractions having GTF activity could be extracted from the cells by the individual extracting procedures and that in order to obtain the extract having high specific activity in high yield, the extracting procedure with 8M urea solution at 25° C. for 1 hour was most appropriate.

EXAMPLE 3

Preparation of CA-GTF-I Purified Preparation

Since the extracting procedure with 8M urea at 25° C. for 1 hour has been revealed to be most appropriate, S. mutans MT8148 was cultivated in TTY medium (8 liters) in the same manner as described in Example 2, and the cells obtained were harvested, washed and then suspended in 300 ml of 8M urea solution. The amount of the cultured cells was 9.7 g by dry weight.

Subsequently, the suspension was subjected to extraction at 25° C. for 1 hour with starring.

After the extraction, the supernatant was obtained by centrifugation to remove cells from the extracting solution and then dialyzed against 10 mM phosphate buffer (pH 6.0).

After the dialysis, insoluble substances produced in the supernatant were removed by centrifugation so as to obtain a CA-GTF-I crude extracted preparation.

Subsequently, ammonium sulfate was added to the CA-GTF-I crude extracted preparation to give 60% saturation to get precipitate. The precipitate was dissolved further in 20 ml of 50 mM phosphate buffer (pH 7.5), and the resultant solution was dialyzed against 50 ml of phosphate buffer (pH 7.5).

After the dialysis, insoluble substances produced during the dialysis were removed from the solution by centrifugation, and the resultant supernatant fluid was applied to a column (2.5×13 cm) of DEAE-SEPHACEL (Pharmacia).

The fractions adsorbed on the column were selectively eluted with a linear concentration gradient of NaCl in phosphate buffer (pH 7.5).

Each of the fractions was assayed for the GTF activity by the method described in Example 1 and for the protein concentration by measuring UV absorbance at 280 nm. Thus, as shown in FIG. 1, marked GTF activity was found in the fractions with the NaCl concentration of 0.45 to 1.0M.

Eluted fractions of the NaCl concentration of 0.45 to 1.0M were pooled, dialyzed against 10 mM phosphate buffer (pH 6.0) and then applied to a column (1.0×13 cm) of hydroxylapatite (BIO-GEL HTP, Bio-Rad Laboratories) previously equilibrated with 10 mM phosphate buffer (pH 6.0).

Fractions adsorbed on the column were eluted stepwise with 0.01M, 0.2M, 0.26M and 0.5M phosphate buffer (pH 6.0).

Figure 2:
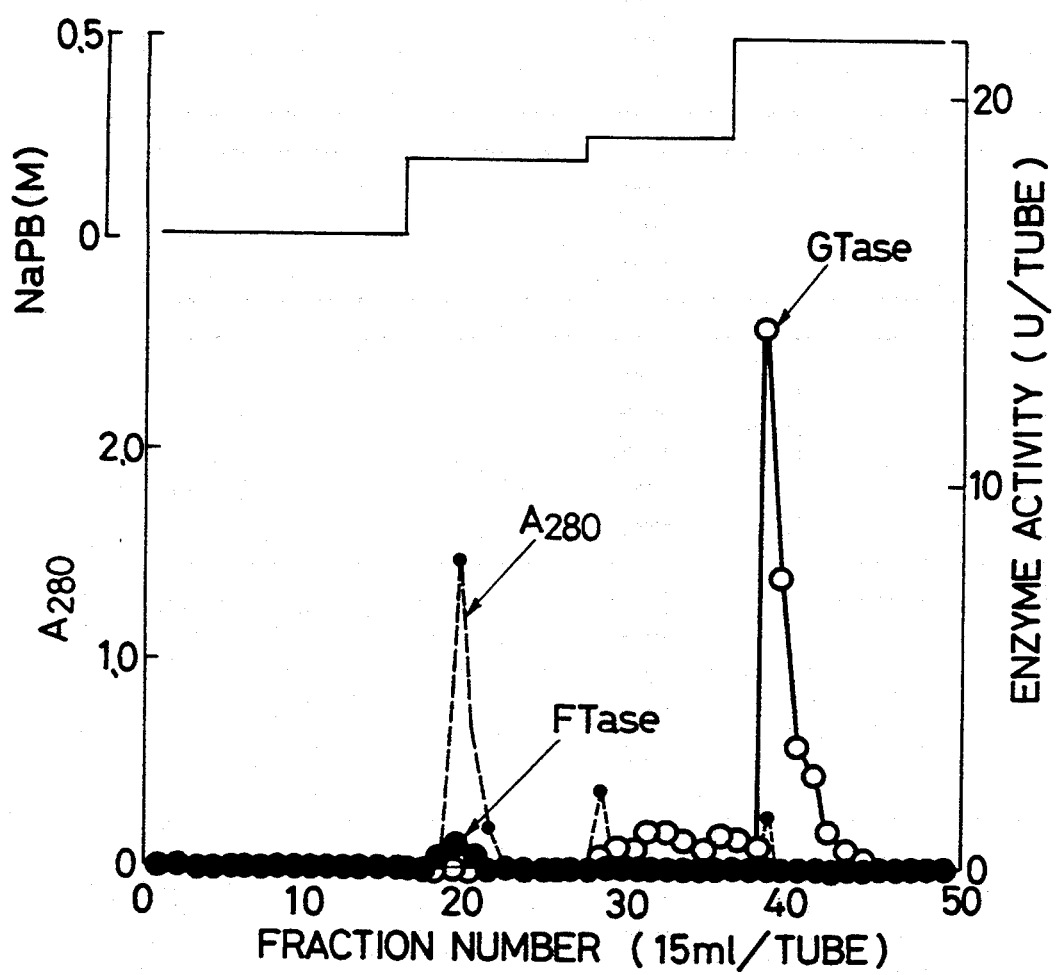
FIG. 2 shows the protein concentration ($A_{280}$), GTF activity and FTase activity in the factions eluted from hydroxylapatite in Example 3.

Each of the fractions was assayed for the GTF activity and protein concentration as described above. As shown in FIG. 2, the GTF activity was found in the fractions eluted with 0.5M phosphate buffer.

Subsequently, the highly active fractions eluted with 0.5M phosphate buffer were pooled and dialyzed against 10 mM phosphate buffer (pH 6.0) to prepare the purified enzyme preparation.

Further, Table 3 shows the GTF activity, protein content, specific GTF activity and yield in the GTF-active fractions obtained in the individual steps of extraction and purification procedures described above.

TABLE 3

| Purification step | Total protein (mg) | Total activity (U) | Specific activity (U/mg) | Recovery (%) | Purification (-fold) |
|---|---|---|---|---|---|
| 8M Urea extract | 207 | 471 | 2.01 | 100 | 1 |
| Ammonium sulfate (60% saturation) | 119 | 260 | 2.18 | 62 | 1.1 |
| DEAE-SEPHACEL | 37.4 | 85.9 | 2.30 | 21 | 1.1 |
| Hydroxylapatite | 4.71 | 32.8 | 6.96 | 8 | 3.5 |

Furthermore, when this purified enzyme preparation was applied on SDS-PAGE (in which proteins were stained by Coomassie Brilliant Blue) under the conditions described below, a single band at the position of a molecular weight of 156 k daltons was observed, which confirmed that the purified enzyme preparation is an enzyme protein having a molecular weight of 156 k daltons. Conditions for SDS-PAGE procedure:

SDS-PAGE was carried out by the method of Laemmli et al.

Namely, the crude extracted preparation and the purified enzyme preparation (0.2 to 35 micrograms) were individually treated with 62.5 mM Tris-HCl buffer (pH 6.8) containing 2% SDS, 5% 2-mercaptoethanol and 20% glycerol at 100° C. for 3 minutes.

The electrophoresis was carried out on 7.5% acrylamide separating gel containing 0.1% SDS and on 4% acrylamide stacking gel at room temperature at 10 mA for 2 hours.

Further, molecular weight standards used were ferritin (220 k daltons), phosphorylase (94 k daltons), bovine serum albumin (67 k daltons), catalase (60 k daltons), ovalbumin (43 k daltons) and lactate dehydrogenase (36 k daltons) (all obtained from Pharmacia).

The purified enzyme preparation in the amount corresponding to 50 mU enzyme activity was added to 0.1M phosphate buffer (pH 6.0) containing 1% sucrose and 0.1% sodium azide (each as final concentrations). Then, the admixture was made to a total volume of 3 ml with distilled water, mixed and then allowed to react at 37° C. for 18 hours. Further, the enzyme reaction was terminated by cooling the reaction solution with ice to 4° C.

After completion of the enzyme reaction, the reaction product was centrifuged at 1,600×g and the water-insoluble precipitated fraction and the supernatant were separated.

The water insoluble fraction was washed twice with distilled water and then suspended in 3 ml of distilled water to obtain a water-insoluble glucan preparation.

Furthermore, 2.5 volumes of ethanol was added to the supernatant, and after the admixture was allowed to stand at 4° C. for 1 hour, the precipitate produced was recovered by centrifugation at 1,600×g and dissolved in 3 ml of distilled water. Further, the precipitation procedure was similarly repeated and the recovered precipitate was again dissolved in 3 ml of distilled water to obtain a water-soluble glucan preparation.

Furthermore, the glucans contained in these preparations were quantitatively analyzed by anthrone method and the kinds of glucans synthesized by the purified enzyme preparation were investigated. As a result, it was revealed that the purified enzyme preparation is a CA-GTF-I having a capability to synthesize water-insoluble glucans.

Separately, the above enzyme reaction was repeated and the resultant water-insoluble glucan precipitate was then separated by centrifugation. After washing of the precipitate (2 mg), it was totally methylated by the method of Hakomori (Hakomori, S., J. Biochem., 55, 205, 1964) and hydrolyzed with 90% (v/v) formic acid and subsequently with 2 M trifluoro-acetic acid. The resultant hydrolyte was reduced in the presence of sodium borohydride and acetylated in a pyridine-acetic anhydride mixture (1:1, v/v) to obtain partially-methylated alditol acetate derivatives. Then, the resulting derivatives were analyzed by a gas chromatograph analyzer (Model: GC-14A, Shimadzu Works) combined with a capillary column (0.25 mm×30 m) coated with silicon SPB-5 (Shimadzu works). Alditol acetate derivatives of dextran T10 (Pharmacia) were also prepared by the same method as described above and used as standard samples.

The results of the analysis indicated that the water-insoluble glucan obtained in the above procedure contained 62 mol % alpha-1,3 linked-, 28% alpha-1,6 linked- and 5% alpha-1,3,6 linked-glucose residues.

Furthermore, by changing the temperature and pH in determining GTF activity as described in Example 1, the temperature optimum and pH optimum for the purified enzyme preparation in water-insoluble glucan synthesizing enzyme activity were investigated.

Furthermore, its Km value was also determined by an ordinary method.

Data obtained by the measurements and tests described above are given in Table 4.

Further, for comparison, Table 4 also includes the corresponding data for CF-GTF-S obtained by the method of Baba et al. (Carbohydr. Res., 158, 147–155, 1986) from the supernatant of S. mutans MT8148 culture cultivated in a medium containing dialyzed BHI.

TABLE 4

| Property | CF-GTF-S | CA-GTF-I |
| --- | --- | --- |
| Molecular weight (average) | 156k | 156k |
| pI | 7.4 | n.d.* |
| pH optimum | 5.5–6.5 | 6.7–7.0 |

TABLE 4-continued

| Property | CF-GTF-S | CA-GTF-I |
| --- | --- | --- |
| Km value for sucrose (mM) | 17.3 | 11.1 |
| Solubility of product glucan in water | Water-soluble | Water-insoluble |

*The measurement was not possible because of extensive aggregation formed in the gel.

Furthermore, it was confirmed by immunoblotting with the antiserum prepared from mice immunized with CA-GTF-I of the present invention that the antibody capable of reacting with the CA-GTF-I of the present invention was obtained in the antiserum.

On the other hand, antigenic properties of the CA-GTF-I and CF-GTF-S obtained in the procedures described above were investigated by using ELISA method. For this purpose, the mouse antiserum against CA-GTF-I was prepared from the mice immunized by cutaneous injection of CA-GTF-I, obtained from strain MT8148, with Freund's complete adjuvant (FCA), and the monoclonal antibody which reacts with water-soluble glucan synthesizing enzyme that was prepared from the supernatant of the strain MT8148 culture by the method of Sato et al. (Sato, S., Koga, T. and Inoue, M., Carbohydr. Res., 134, 293–304, 1984). Further, alkali-phosphatase-labeled goat anti-mouse IgA+IgG+IgM antibody was used as a second antibody and p-nitrophenylphosphate disodium was used as a substrate. The results are given in Table 5. Namely, it was revealed that the mouse antiserum against CA-GTF-I did not react with CF-GTF-S and that the monoclonal antibody against CF-GTF-S did not react with CA-GTF-I, which evidenced that these enzymes had different antigenicity.

TABLE 5

| | Absorbance at 405 nm | |
| --- | --- | --- |
| Coating antigen | Monoclonal antibody against anti-CF-GTF-S | Antiserum against anti-CA-GTF-I |
| CF-GTF-S | | |
| Crude | 0.336 | 0.066 |
| Purified | 0.890 | 0.045 |
| CA-GTF-I | | |
| Crude | 0.125 | 0.356 |
| Purified | 0.054 | 0.666 |

EXAMPLE 4

Preparation of antigen

S. mutans strain Ingbritt (serotype c, obtained from the Department of Dentistry, Osaka University) was cultivated in 15 liters of TTY medium at 37° C. for 18 hours and the cultured cells thus obtained were washed twice with saline.

Then, the washed cells were suspended in 400 ml of 8M urea solution and the cell suspension was stirred at 25° C. for 1 hour. The cell suspension was then centrifuged to remove the cells and the resultant supernatant was dialyzed against 10 mM phosphate buffer (pH 6.0).

After the dialysis, the precipitate produced in the supernatant was removed by centrifugation and the resultant supernatant was precipitated with ammonium sulfate at 60% saturation. The obtained precipitate was recovered by centrifugation. The precipitate was then dissolved in 10 mM phosphate buffer (pH 6.0) and the resultant solution was dialyzed against the same buffer. Further, the precipitate appeared in the solution was removed by centrifugation to obtain a supernatant. The supernatant was used as a crude (immuno-antigen) preparation.

The protein concentration and total protein of the preparation were measured by CBB-G method (Branford, M. M., Anal. Biochem., 72, 248, 1976), so that it was revealed that the protein concentration was 5.1 mg/ml and the amount of total protein was 141 mg.

Furthermore, the preparation was applied on SDS-polyacrylamide gel electrophoresis (SDS-PAGE) under the conditions as described in Example 3, and the staining with Coomassie Brilliant Blue (CBB) was carried out. As a result, several bands including the band corresponding to the position for 155 k daltons were identified.

Separately, the preparation was treated in Tris-HCl buffer at 37° C. for 30 minutes and subjected to SDS-PAGE in the same manner as described above except that the temperature for the electrophoresis was 4° C. The resultant gel was immersed in phosphate buffer (pH 6.0) containing 1% sucrose and 0.05% sodium azide at 37° C. for 18 hours. Then, the immersed gel was taken out and stained with PAS (Periodicacid Schiff) reagent. As a result, a distinctly stained band demonstrating the production of glucans was identified at the position of 155 k daltons.

Further, the CA-GTF-I content of the preparation calculated from the results of the SDS-PAGE described above was 40% by weight.

EXAMPLE 5

Preparation of purified CA-GTF-I preparation

The strain Ingbritt was cultivated in TTY medium (8 liters) under the same conditions as described in Example 4. The resultant cells were harvested, washed and then suspended in 300 ml of 8M urea solution.

Then, the suspension was stirred at 25° C. for 1 hour for extraction.

After the extraction, the extracting solution was centrifuged to remove cells and the resultant supernatant was dialyzed against 10 mM phosphate buffer (pH 6.0).

After the dialysis, the precipitate produced in the supernatant was removed to obtain a CA-GTF-I crude extracted preparation.

Then, ammonium sulfate was added to the crude extracted preparation to 60% saturation to get precipitate. The resultant precipitate was further dissolved in 20 ml of 50 mM phosphate buffer (pH 7.5) and then dialyzed against the same buffer.

After the dialysis, the precipitate produced during the dialysis was removed by centrifugation. The resultant supernatant was applied to a column (2.5×13 cm) of DEAE-SEPHACEL (Pharmacia).

The fractions adsorbed on the column were selectively eluted with a linear concentration gradient of NaCl in phosphate buffer (pH 7.5).

The GTF activities of the eluted each fractions were measured as described in Example 1 and the protein concentrations were determined by measuring UV absorbance at 280 nm. As a result, markedly high activities were observed in the fractions eluted with the NaCl concentrations of 0.45 to 1.0M.

The fractions eluted with the NaCl concentrations of 0.45 to 1.0M were then pooled, dialyzed against 10 mM phosphate buffer (pH 6.0) and then applied to a column (1.0×13 cm) of hydroxylapatite (BIO-GEL HTP, Bio-Rad Laboratories) which had been equilibrated with 10 mM phosphate buffer (pH 6.0).

Fractions adsorbed on the column were eluted stepwise with 0.01M, 0.2M, 0.26M and 0.5M phosphate buffer (pH 6.0).

The GTF activity and protein concentration of each of the fractions were determined by the method described above. As a result, the GTF activity was found in the factions eluted with 0.5M phosphate buffer (pH 6.0).

Then, the highly active fractions eluted with 0.5M phosphate buffer (pH 6.0) were pooled and dialyzed against 10 mM phosphate buffer (pH 6.0) to obtain a purified enzyme preparation.

Furthermore, the purified enzyme preparation was applied to SDS-PAGE under the aforementioned conditions and proteins were stained with CBB. As a result, a single band was detected on the position corresponding to a molecular weight of 155 k daltons, which confirmed that the purified enzyme preparation is an enzyme protein having a molecular weight of 155 k daltons.

Further, the conditions for the GTF measurements as described in Example 1 were modified so as to investigate the purified enzyme preparation in terms of pH optimum of the GTF activity, temperature optimum range for the reaction and conditions for inactivation. As a result it was confirmed that the purified enzyme preparation obtained had the physicochemical characteristics of (2) to (4) thereinbefore described.

Furthermore, the kind of glucans synthesized by the action of the purified enzyme preparation was investigated according to the method described in Example 3 by using the purified enzyme preparation in the amount corresponding to 50 mU enzyme activity. As a result, it was revealed that the purified enzyme preparation was CA-GTF-I having the activity to synthesize water-insoluble glucans.

Further, the amount of the protein of the resultant purified enzyme preparation was measured by the method described above. The amount was 9.7 mg.

EXAMPLE 6

Preparation of Antibody

A W/O type emulsion was prepared by mixing 0.5 ml of the crude CA-GTF-I preparation (containing 1 mg of protein according to the measurement by the CBB-B method) obtained in Example 4 and 0.5 ml of FCA (Freund's complete adjuvant) in 1:1 ratio.

The first immunization was made by injection of 0.5 ml each of the emulsion to the right and left sides of the breast muscle of hens. Thereafter, the antibody titer of WSF (explained below) obtained from eggs were measured by the method described below and the changes thereof were observed.

(1) Isolation method of antibody from eggs:

An egg yolk separated from eggs was mixed with the same volume of PBS (phosphate-buffered saline, pH 7.4) and 2 volumes of chloroform.

The mixture was incubated at room temperature for 30 minutes, centrifuged at 3,000 rpm for 20 minutes and then the upper layer was used as WSF (water soluble fraction).

(2) Method of measuring antibody titer:

The measurement of antibody titer was carried out by ELISA.

First, the crude immunizing antigen preparation obtained in example 1 was applied on SDS-PAGE so as to isolate a protein-containing fraction from the portion on the SDS-PAGE corresponding to a molecular weight of 155 k daltons by using an electrical elution method. Further, this fraction was applied to SDS-PAGE, and a single band on the position corresponding to the molecular weight of 155 k daltons was detected by staining the gel with CBB-R 250.

The obtained fraction was dissolved in 50 mM sodium carbonate buffer (pH 9.6) so as to give the protein concentration of 1.25 micrograms/ml. Aliquots of 100 microliters each of the resultant solution were dispensed in each of wells on a 96-well microtiter plate (IMMULON 2, Dynateck) and incubated at 4° C. overnight so that the purified antigen contained in the fraction was coated to the plate.

The plate was then washed 5 times with PBS-T (PBS containing 0.05% TWEEN20) (pH 7.4).

After the washing, the well was blocked with PBS (pH 7.4) containing 3% BSA (bovine serum albumin) at 37° C. for 1 hour and then the plate was washed 5 times with PBS-T.

Then, 100 microliters each of the previously obtained WSF, which had been diluted in two steps with PBS-T, was added to each of the wells and allowed to react at 37° C. for 1 hour.

After completion of the reaction, the plate was washed 5 times with PBS-T and 100 microliters each of peroxidase conjugated anti-chicken IgG antibody (protein content of 1.67 micrograms/ml) was added to each of the wells on the plate. The plate was incubated at 25° C. for 30 minutes and then washed 5 times with PBS-T.

Then, to each of the wells of the plate was added 100 microliters of the solution prepared by dissolution of 20 mg of o-phenylenediamine and 10 microliters of peroxide, as substrates, in 50 ml of 0.2M disodium phosphate-0.1M citric acid buffer (pH 5.0). The reaction was carried out by incubation at 25° C. for 20 minutes and then terminated by addition of 100 microliters of 3N sulfuric acid solution.

After the reaction, antibody titer was measured by the optical density ($OD_{492}$) of the each wells. The antibody titer was estimated by the end point titer method as the dilution that give the optical density of 0.2.

Subsequently, by confirming that the antibody titer in the egg yolk began to decline 8 weeks after the first immunization as shown in FIG. 1, the secondary immunization was conducted in the same manner as previously done.

The eggs were collected about one month after the secondary immunization, and the antibody titer was determined by the method described above.

As a result, WSF having the antibody titer of $8.4 \times 10^3$ was obtained 12 weeks after the first immunization (4 weeks after the secondary immunization).

Further, the protein concentration of the WSF having the antibody titer of $8.4 \times 10^3$ (13 ml, prepared from 13 ml of egg yolk) was measured by Biuret method. As a result, total protein in the WSF was approximately 26 mg (about 2.0 mg/ml × 13 ml).

EXAMPLE 7

Confirmation of inhibition of adherence of *S. mutans* to smooth surfaces by antibody As a model experiment on adherence of *S. mutans* to teeth surfaces, the experiment on adherence to glass surfaces was carried out.

Namely, the experiment was designed to evaluate the extent of inhibition of the adherence of *S. mutans* to the glass surfaces by addition of the antibody obtained in Example 6. The procedures is explained below.

First, the WSF obtained in Example 6, having the antibody titer of $8.4 \times 10^3$, and a 10 time-diluted solution thereof were used as test solutions.

Separately, WSF was prepared from eggs of non-immunized hens (those of the same kinds as used in Example 5) in the same manner as described in Example 6, to be used as a test solution. Further, it was confirmed that this WSF did not specifically react with CA-GTF-I.

Then, portions of 1 ml each of these test solutions were dispensed into test tubes (13 mm$\phi$ × 100 mm), and further portions of 2 ml each of 1.5-fold concentrated BHI medium containing 1.5% sucrose were added to the test tubes.

Further, to each of the test tubes was added 0.1 ml of the suspension of *S. mutans* strain Ingbritt precultivated in BHI medium, and the test tubes, being allowed to decline at the angle of 30°, were statically incubated at 37° C. for 18 hours.

The compositions of the preparations prepared in each of the test tubes are given in Table 6.

After completion of the static incubation, each of the test tubes was treated according to the procedures described below and the rate of adherence of the cells to the wall of the test tubes was determined.

After completion of the static incubation, each of the test tubes (hereinafter referred to as the first test tubes) was allowed to gently rotate, and the whole fluid containing the cells which did not adhere onto the wall of the test tube was transferred to each of the second test tubes. Then, 3 ml each of 50 mM phosphate buffer (pH 6.8) was added to each of the first test tubes with adherent cells on the wall, and the tubes were again allowed to rotate. After the whole buffer solution containing released cells was transferred to each of the third test tubes, 3 ml each of 50 mM phosphate buffer (pH 6.8) was added to each of the resultant first test tubes.

Furthermore, the first, second and third test tubes were subjected to the ultrasonication procedure to prepare homogeneous cell suspensions in each of the test tubes. The optical density ($OD_{550}$) of each of the suspensions was measured and the individual adherence rate was calculated as follows:

$$\text{Adherence rate (\%)} = \frac{\text{Optical density of the 1st test tube}}{\text{Sum of the optical densities of the 1st, 2nd and 3rd test tubes}} \times 100$$

The results obtained are given in Table 6.

TABLE 6

|  | Cell suspension No. | | |
|---|---|---|---|
|  | 1 | 2 | 3 |
| 3/2-fold concentrated BHI medium containing 1.5% sucrose | 2 ml | 2 ml | 2 ml |
| WSF | 1 ml | — | — |
| 10-fold diluted WSF | — | 1 ml | — |
| WSF from eggs of non-immunized hens | — | — | 1 ml |
| Bacterial cells (preculture of *S. mutans* strain Ingbritt in BHI | 0.1 ml | 0.1 ml | 0.1 ml |
| Adherence rate (%) | 26.0 | 65.3 | 89.6 |

EXAMPLE 8

The antibody was prepared in the same manner as described in Example 6 except that the purified CA-GTF-I preparation obtained in Example 5 was used as the antigen. As a result, the antibody similarly capable of reacting specifically with CA-GTF-I was obtained.

Furthermore, the obtained antibody was examined for the preventive effect on bacterial adherence in the same manner as described in Example 7, which confirmed that the obtained antibody similarly had prominent preventive effect.

EXAMPLE 9

The WSF having the antibody titer of $8.4 \times 10^3$, which was obtained in Example 6, were added (0.5% by weight) to the component having the composition given in Table 7 to prepare a tooth paste, and to the solution having the composition given in Table 8 to prepare a mouth wash.

Specifically, a solution prepared by dissolving 1.2 weight % carboxymethylcellulose and 0.1 weight % saccharide sodium in distilled water was added to 42 weight % calcium pyrophosphate to obtain a mixture. To the mixture, 15 weight % glycerol, 10 weight % sorbit, 2.0 weight % sodium lauryl sulfate, 1.0 weight % perfume and 0.5 weight % WSF were further added. The resulting mixture was then fully mixed by a kneader or a mixing agitator and rolled to obtain a tooth paste composition shown in Table 7. After bubbles were removed from the composition, the composition was filled in tubes.

Separately, 1.0 weight % perfume and 0.3 weight % lauryldiethanolamide were dissolved in 22.5 weight % ethanol and, to the resulting solution, a solution prepared by dissolving 0.05 weight % saccharide sodium and 0.5 weight % WSF in distilled water was added to obtain a mixture. Distilled water was further added to the mixture to obtain a mouth wash having the composition shown in Table 8.

TABLE 7

| Constituent | Concentration (% by weight) |
| --- | --- |
| Calcium pyrophosphate | 42 |
| Glycerol | 15 |
| Sorbit (70 %) | 10 |
| Carboxymethylcellulose | 1.2 |
| Saccharine sodium | 0.1 |
| Sodium lauryl sulfate | 2.0 |
| Perfume | 1.0 |
| Water | Rest |
|  | 100% |

TABLE 8

| Component | Concentration (% by weight) |
| --- | --- |
| Ethanol | 22.5 |
| Saccharine sodium | 0.05 |
| Lauryldietrianolamide | 0.3 |
| Perfume | 1.0 |
| Water | Rest |
|  | 100% |

What is claimed is:

1. A composition for topical use to prevent adherence of *Streptococcus mutans* cells on tooth surfaces, which comprises:

(i) an effective amount of an egg yolk antibody obtained by the steps of:

(A) cultivating cells of *Streptococcus mutans* serotype c, e, or f in a nutrient-containing culture medium to obtain a culture containing cultured cells;

(B) removing the supernatant from the culture to recover the cultured cells;

(C) extracting a glucosyltransferase from the cultured cells using a urea or guanidine-HCl solution and purifying the glucosyltransferase, said purified glucosyltransferase having the following physicochemical characteristics:

(a) capable of catalyzing the synthesis of water-insoluble glucan from sucrose;

(b) having an optimum pH between 6.7 and 7.0 for catalyzing the synthesis of water-insoluble glucan from sucrose;

(c) losing its activity by heat treatment at 80° C. for 5 minutes;

(d) having a molecular weight of 150 to 165 kilodaltons as determined by SDS-polyacrylamide gel electrophoresis; and (e) antigenic in animals and capable of raising an antibody specifically binding to the glucosyltransferase;

(D) immunizing hens with the purified glucosyltransferase; and (E) separating the egg yolk antibody, which specifically binds to the glucosyltransferase, from the eggs of the immunized hens; and (ii) a physiologically acceptable diluent or carrier.

2. The composition of claim 1 in which the urea solution is a 6–10M urea solution and the guanidine-HCl solution is a 6M guanidine-HCl solution.

3. The composition of claim 2 in which the urea solution is an 8M urea. solution.

4. The compostion of claim 1 in which the glucosyltransferase is purified with an anion-exchange resin and hydroxylapatite.

5. A composition for topical use to prevent adherence of *Streptococus mutans* cells on tooth surfaces, which comprises;

(i) an effective amount of an egg yolk antibody obtained by the steps of:

(A) cultivating cells of *Streptococcus mutans* serotype c, e or f in a nutrient-containing culture medium to obtain a culture containing cultured cells;

(B) removing the supernatant from the culture to recover the cultured cells;

(C) contacting the cultured cells with a urea or guanidine-HCl solution to extract a glucosyltransferase from the cultured cells and thus form an extract containing the glucosyltransferase;

(D) removing urea or guanidine-HCl from the extract to obtain a glucosyltransferase preparation including the glucosyltransferase, which has the following physicochemical characteristics, when the glucosyltransferase is purified:

(a) capable of catalyzing the synthesis of water-insoluble glucan from sucrose;

(b) having an optimum pH between 6.7 and 7.0 for catalyzing the synthesis of water-insoluble glucan from sucrose;

(c) losing its activity by heat treatment at 80° for 5 minutes;

(d) having a molecular weight of 150 to 165 kilodaltons as determined by SDS-polyacrylamide gel electrophoresis; and (e) antigenic in animals and capable of raising an antibody specifically binding to the glucosyltransferase;

(E) immunizing hens with the glucosyltransferase preparation; and (F) separating the egg yolk antibody, which specifically binds to the glucosyltransferase, from the eggs of the immunized hens; and (ii) a physiologically acceptable diluent or carrier.

6. The composition of claim 5 in which the urea solution is a 6–10M urea solution and the guanidine-HCl solution is a 6M guanidine-HCl solution.

7. The composition of claim 6 in which the urea solution is an 8M urea solution.

8. The composition of claim 5, 6 or 7 in which urea or guanidine HCl is removed from the extract by dialysis.

9. A method of preventing adherence of *Streptococcus mutans* cells on tooth surfaces comprising topically applying an effective amount of an egg yolk antibody to the mouth of a person requiring the same, said egg yolk antibody being obtained by the steps of:

(A) cultivating cells of *Streptococcus mutans* serotype c, e or f in a nutrient-containing culture medium to obtain a culture containing cultured cells;

(B) removing the supernatant from the culture to recover the cultured cells;

(C) extracting a glucosyltransferase from the cultured cells using a urea or guanidine-HCl solution and purifying the glucosyltransferase, said glucosyltransferase having the following physicochemical characteristics:

(a) capable of catalyzing the synthesis of water-insoluble glucan from sucrose;

(b) having an optimum pH between glucan 6.7 and 7.0 for catalyzing the synthesis of water-insoluble glucan from sucrose;

(c) losing its activity by heat treatment at 80° C. for 5 minutes;

(d) having a molecular weight of 150 to 165 kilodaltons as determined by SDS-polyacrylamide gel electrophoresis; and (e) antigenic in animals and capable of raising an antibody specifically binding to the glucosyltransferase;

(D) immunizing hens with the purified glucosyltransferase; and (E) separating the egg yolk antibody, which specifically binds to the glucosyltransferase, from the eggs of the immunized hens.

10. The method of claim 9 in which the urea solution is a 6–8M urea solution and the guanidine-HCl solution is a 6M guanidine-HCl solution.

11. The method of claim 10 in which the urea solution is an 8M urea solution.

12. The method of claim 9 in which glucosyltransferase is purified with an anion-exchange resin and hydroxylapatite.

13. A method of preventing adherence of *Streptococcus mutans* cells on tooth surfaces comprising topically applying an effective amount of an egg yolk antibody to the mouth of a person requiring the same, said egg yolk antibody being obtained by the steps of:

(A) cultivating cells of *Streptococcus mutans* serotype c, e or f in a nutrient-containing culture medium to obtain a culture containing cultured cells;

(B) removing the supernatant from the culture to recover the cultured cells;

(C) contacting the cultured cells with a urea or guanidine-HCl solution to extract a glucosyltransferase from the cultured cells and thus form an extract containing the glucosyltransferase;

(D) removing urea or guanidine-HCl from the extract to obtain a glucosyltransferase preparation including the glucosyltransferase, which has the following physiochemical characteristics, when the glucosyltransferase is purified:

(a) capable of catalyzing the synthesis of water-insoluble glucan from sucrose;

(b) having an optimum pH between 6.7 and 7.0 for catalyzing the synthesis of water-insoluble glucan from sucrose;

(c) losing its activity by heat treatment at 80° C. for 5 minutes;

(d) having a molecular weight of 150 to 165 kilodaltons as determined by SDS-polyacrylamide gel electrophoresis; and (e) antigenic in animals and capable of raising an antibody specifically binding to the glucosyltransferase;

(E) immunizing hens with the glucosyltransferase preparation; and (F) separating the egg yolk antibody, which specifically binds to the glucosyltransferase, from the eggs of the immunized hens.

14. The method of claim 13 in which the urea solution is a 6–10M urea solution or the guanidine-HCl solution is a 6M guanidine-HCl solution.

15. The method of claim 14 in which the urea solution is an 8M urea solution.

16. The method of claim 13, 14 or 15 in which urea or guanidine-HCl is removed from the extract by dialysis.

* * * * *